US011576557B2

(12) United States Patent
Regensburger

(10) Patent No.: US 11,576,557 B2
(45) Date of Patent: Feb. 14, 2023

(54) METHOD FOR SUPPORTING A USER, COMPUTER PROGRAM PRODUCT, DATA MEDIUM AND IMAGING SYSTEM

(71) Applicant: Siemens Healthcare GmbH, Erlangen (DE)

(72) Inventor: Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 676 days.

(21) Appl. No.: 16/572,414

(22) Filed: Sep. 16, 2019

(65) Prior Publication Data

US 2020/0085281 A1    Mar. 19, 2020

(30) Foreign Application Priority Data

Sep. 19, 2018    (EP) ..................................... 18195330

(51) Int. Cl.
*A61B 6/00*    (2006.01)
*A61B 1/00*    (2006.01)
(Continued)

(52) U.S. Cl.
CPC ........ *A61B 1/0005* (2013.01); *A61B 1/00009* (2013.01); *A61B 1/00193* (2013.01);
(Continued)

(58) Field of Classification Search
CPC combination set(s) only.
See application file for complete search history.

(56) References Cited

U.S. PATENT DOCUMENTS

2009/0088632 A1* 4/2009 Khamene ............... G06T 7/75
    600/424
2009/0088773 A1* 4/2009 Zhao ...................... A61B 34/37
    606/130
(Continued)

FOREIGN PATENT DOCUMENTS

DE    102016202512 B3    8/2017
DE    102017216953 A1    3/2019
(Continued)

OTHER PUBLICATIONS

Communication under Rule 71(3) EPC for European Application No. 18 195 330.8-1122 dated Aug. 27, 2020.
(Continued)

*Primary Examiner* — Joel F Brutus
(74) *Attorney, Agent, or Firm* — Lempia Summerfield Katz LLC

(57) ABSTRACT

A method for supporting a user, a corresponding computer program product, a corresponding data medium, and a corresponding imaging system are provided. According to the method, a three-dimensional (3D) data set depicting a target object is provided, and at least one two-dimensional (2D) image of the target object is automatically acquired. The 2D image and the 3D data set are automatically registered with each other by a 2D/3D registration. A spatial direction in which the 2D/3D registration exhibits greatest uncertainty is automatically specified. A signal for aligning an instrument that is provided for the purpose of examining the target object is then automatically generated and output as a function of the specified spatial direction in order to support the user.

17 Claims, 1 Drawing Sheet

(51) Int. Cl.
  *G06T 7/30* (2017.01)
  *A61B 6/12* (2006.01)
  *A61B 10/04* (2006.01)
  *G06T 7/20* (2017.01)

(52) U.S. Cl.
  CPC .............. *A61B 6/12* (2013.01); *A61B 6/4441* (2013.01); *A61B 6/5223* (2013.01); *A61B 10/04* (2013.01); *G06T 7/20* (2013.01); *G06T 7/30* (2017.01); *A61B 2010/045* (2013.01); *G06T 2207/10116* (2013.01); *G06T 2207/30004* (2013.01)

(56) References Cited

U.S. PATENT DOCUMENTS

| | | | |
|---|---|---|---|
| 2012/0165655 A1* | 6/2012 | Mucha | A61B 34/30 600/300 |
| 2012/0289825 A1* | 11/2012 | Rai | A61B 6/547 600/425 |
| 2015/0030229 A1 | 1/2015 | Borsdorf | |
| 2015/0085981 A1 | 3/2015 | Siewerdsen | |
| 2016/0260220 A1 | 9/2016 | Liu | |
| 2017/0165008 A1 | 6/2017 | Finley | |
| 2017/0172663 A1 | 6/2017 | Popovic et al. | |
| 2017/0209071 A1 | 7/2017 | Zhao et al. | |
| 2017/0243361 A1 | 8/2017 | Schaffert | |
| 2018/0150929 A1 | 5/2018 | Pheiffer | |
| 2019/0096084 A1 | 3/2019 | Mayer | |

FOREIGN PATENT DOCUMENTS

| | | |
|---|---|---|
| JP | 2009056238 A | 3/2009 |
| JP | 2017507708 A | 3/2017 |
| JP | 2017086819 A | 5/2017 |
| JP | 2017523836 A | 8/2017 |
| WO | WO2008120136 A1 | 10/2008 |
| WO | WO2016182550 A1 | 11/2016 |

OTHER PUBLICATIONS

European Decision to Grant for European Application No. 18195330.8-1122 / 3626176 dated Dec. 3, 2020.
European Search Report for European Application No. 18195330.8-1124 dated Mar. 28, 2019.
Japanese Office Action for Japanese Application No. 2019-128017 dated Apr. 6, 2021, with English translation.
European Search Report for European Patent Application No. 18195330.8-1124 dated Mar. 28, 2019.

* cited by examiner

METHOD FOR SUPPORTING A USER, COMPUTER PROGRAM PRODUCT, DATA MEDIUM AND IMAGING SYSTEM

This application claims the benefit of EP 18195330.8, filed on Sep. 19, 2018, which is hereby incorporated by reference in its entirety.

BACKGROUND

The present embodiments relate to supporting a user.

There nowadays exists a multiplicity of different imaging modalities, these being employed in a medical environment, for example, but likewise also in other industrial fields for the purpose of depicting a respective target object or examination object. A technique that is nowadays widely used in this case combines data from different sources, where the corresponding data (e.g., images or data sets) are registered with each other so that the images or data sets may be overlaid in a positionally accurate manner within a shared coordinate system. In order that a respective situation may be recognized and evaluated as accurately and reliably as possible, or in order that the depicted examination object may be, for example, manipulated as accurately and reliably as possible, maximal precision of the registration is desirable. Errors, inaccuracies, or uncertainties in the registration may have disadvantageous consequences, accordingly.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a user may be supported in situations where there is an erroneous or uncertain registration.

A method according to one or more of the present embodiments is used to support a user, for example, when examining an examination object or target object. According to the method, a three-dimensional (3D) data set depicting the target object is first provided. The provision may in this case include or signify, for example, providing or making available a data store on which the 3D data set is stored. Equally, the provision may signify or include acquiring or recording (e.g., measuring) the 3D data set.

The 3D data set may be recorded or have been recorded, for example, by a first imaging modality (e.g., by a computed tomograph, such as a computed tomography (CT) X-ray device, a magnetic resonance (MR) installation, or similar).

The target object may be, for example, a patient, part of a patient, a specific organ, or a tissue sample, but also ultimately, any object or material that may be depicted by a corresponding imaging modality. For example, it is normal practice in industrial application fields for technical devices to be depicted and examined by X-radiation. The 3D data set may be a set (e.g., a collection of measured values or data points) or a 3D image, for example.

According to the method according to one or more of the present embodiments, at least one two-dimensional (2D) image of the target object is also acquired. This acquisition may include or signify, for example, a retrieval of the 2D image (e.g., corresponding data) from a data store that is provided, or equally a measurement or recording of the 2D image. The recording of the 2D image may be effected automatically, for example, or possibly triggered by activation of a foot switch or similar. For example, the 2D image may be recorded or have been recorded by a second imaging modality. The second imaging modality may correspond to the first imaging modality in this case, or differ therefrom (e.g., variously). In one embodiment, the first imaging modality may be a 3D X-ray device, and the second imaging modality may be a 2D X-ray device or the 3D X-ray device operated in a 2D mode.

According to the method of one or more of the present embodiments, provision is also made for automatically performing a 2D/3D registration of the at least one 2D image with the 3D data set that is provided. In other words, the 2D image and the 3D data set are therefore combined together or overlaid on each other in a positionally accurate manner (e.g., arranged in a shared coordinate system such that respective mutually corresponding parts or regions of the depicted target object overlap each other in the 2D image and the 3D data set in a corresponding overlay). The 2D image in this case may be arranged in three spatial dimensions or directions in space, which are also referred to as x, y, and z in the following. According to the method of one or more of the present embodiments, provision is also made for automatically specifying one of these spatial directions in which the 2D/3D registration has the greatest uncertainty or inaccuracy (e.g., greatest error). The uncertainty or inaccuracy of the registration is therefore greater in the specified spatial direction than in the two other spatial directions.

Known methods for 2D/3D registration are often not equally precise in all three spatial directions. For example, it is frequently observed that the 2D/3D registration takes place with a relatively high degree of precision or accuracy in two orthogonal spatial directions (e.g., x and y), but may only be performed relatively inaccurately (e.g., with significantly less precision or accuracy in the third spatial direction, such as in the z-direction). This may occur or may be the case, for example, if a recording direction of the 2D image (e.g., a corresponding radiation direction or projection direction of the X-ray device) extends along the z-direction or z-axis. In other words, the recording direction of the 2D image may therefore be specified as the spatial direction in which the 2D/3D registration has greatest uncertainty. The uncertainty or inaccuracy of the 2D/3D registration is therefore ultimately due to a relatively low or inadequate depth resolution of the 2D image. The spatial direction of greatest uncertainty of the 2D/3D registration (e.g., of greatest registration uncertainty) may be effected in this case by, for example, recognizing or tracking a pose of the X-ray device that is used to record the 2D image and of the target object. From corresponding data, it is then possible directly or, for example, by a corresponding object recognition algorithm or image processing algorithm, possibly with reference to further sensor data and/or user inputs, to automatically specify the recording direction for the 2D image (e.g., an angle of a corresponding axis in the shared coordinate system or in a coordinate system of the 3D data set).

According to the method according to one or more of the present embodiments, a signal for aligning or for supporting the alignment of an instrument that is provided for the purpose of examining the target object is also generated and output as a function of the specified spatial direction of greatest uncertainty in order to support the user. The user may therefore be, for example, an operator of the X-ray device and/or the instrument (e.g., a doctor or a technician). The alignment of the instrument or the support of the alignment may signify that the instrument itself may be moved or repositioned in this case or for this purpose. The alignment may equally signify that another object (e.g., an imaging device, a patient couch, or similar) may be moved or repositioned, thereby producing a new or adapted relative alignment of the instrument (e.g., the alignment thereof relative to the object that is actually moved or repositioned). In the following, the "alignment" may be a direct or relative alignment or, if applicable, the corresponding support of the alignment likewise.

The instrument may be, for example, a camera, a sensor, a needle, a probe, or one of a plurality of similar or further instruments or devices. A number of examples concerning this are explained in greater detail below.

The signal may be, for example, an acoustic, optical, and/or haptic indication, a graphical representation, a data signal or data set, a control signal, and/or similar. This is likewise explained in greater detail below. By or by virtue of the signal, data or information is ultimately therefore provided to the user, and/or a measure or a process is initiated. The user is advantageously able, for example, to evaluate a respective situation (e.g., the target object) more accurately and/or more reliably, and/or the user is at least informed of the uncertainty of the 2D/3D registration and therefore, if applicable, a corresponding alignment, positioning, and/or effect of the instrument in the specified spatial direction.

In existing applications, a corresponding registration uncertainty is often simply accepted as unavoidable. Alternatively, for example, during an examination of the target object, a multiplicity of further images, depictions, or data of the target object is recorded instead of the 2D image in order to obtain sufficient data for a more accurate registration in all spatial directions. However, this may disadvantageously result in a higher dosage or exposure of the target object as well as a time delay and/or logistical difficulties or collision problems in a workflow during the depiction or examination of the target object. In addition, a correspondingly more sophisticated and hence more expensive imaging system (e.g., a corresponding X-ray device) may be provided in order not only to record the 3D data set but also when examining the target object. In addition, a registration uncertainty of which the respective user is not aware or conscious conceals a danger of erroneous decisions that render a result of the respective examination of the target object worthless or questionable and/or may injure or damage the target object. These disadvantages may be avoided or lessened by the present embodiments.

In an embodiment, an endoscope (e.g., a camera or an image recording device, such as a laparoscope) is used as the instrument. A pose (e.g., a position and orientation) of the endoscope in a coordinate system of the 3D image and/or the 2D image is then automatically tracked, if applicable, up to a predetermined (e.g., known) transformation of coordinates. Therefore, if the same coordinate system is not used for recording the 2D image and for positioning the endoscope, the two coordinate systems at least have a predetermined spatial location relationship to each other. This may be provided, for example, by corresponding measurement or calibration in advance. At least one overlay image is then generated from at least one endoscope image of the target object, as recorded by the endoscope, and the 3D data set. If a stereo endoscope is used, for example, it is possible correspondingly to use two endoscope images (e.g., the two partial stereo images) and correspondingly to generate two overlay images, for example.

Since there may be a significant time period between the recording of the 3D data set and the recording of the endoscope image (e.g., a plurality of hours or days) and the target object accordingly may have moved meanwhile in an unknown manner, the 2D/3D registration is used in order to generate the overlay image in a positionally accurate manner (e.g., in order to overlay the endoscope image and the 3D data set with positional accuracy). With reference to the 2D image, a respectively current pose of the target object may therefore be specified and related to the 3D data set or to a coordinate system of the 3D data set. Using the known location relationship of the coordinate systems of the 2D image and the endoscope or endoscope image, it is then possible correspondingly to specify a location relationship between the endoscope image and the 3D data set or a location relationship of the corresponding coordinate systems.

In order to obtain the overlay image, the endoscope image and the 3D data set may be overlaid on each other in this case. However, the endoscope image may equally be combined (e.g., overlaid) with a representation or structure that is generated or derived from the 3D data set (e.g., a virtual model or a segmentation grid or a segmented representation). The endoscope image may therefore be, for example, a camera image or a video that depicts the target object in a manner that is optically realistic (e.g., true to reality). The overlay image may be conceived or generated as augmented reality, accordingly.

An indication to the user is then output as the signal or as part of the signal, indicating that and how the user may change the alignment of the endo scope such that an acquisition direction of the endoscope extends at least substantially along the specified spatial direction of greatest registration uncertainty, such that a visualization error caused by the uncertainty of the 2D/3D registration is reduced in the overlay image.

The acquisition direction of the endoscope corresponds in this case to an optical axis of the endoscope, and to that direction in or along which a central ray of a light pencil that is acquired by the endoscope is, for example, acquired. The acquisition direction of the endoscope may therefore be, for example, orthogonal to an image plane of the endoscope image. The alignment of the endoscope or the acquisition direction of the endoscope along the specified spatial direction may signify in this case an at least substantially parallel or antiparallel alignment.

For example, if only one 2D image is used for the 2D/3D registration, the acquisition direction of the endoscope may then be aligned along the recording direction of this one 2D image.

The alignment of the endoscope or the acquisition direction thereof, at least substantially along the specified spatial direction, may signify a corresponding alignment up to errors or deviations of, for example, 10° in this case. The specified spatial direction of greatest uncertainty of the 2D/3D registration then coincides at least substantially with an observation direction or depth direction of the overlay image. Although the uncertainty may still exist, experience shows that the uncertainty is perceived as less disruptive by an observer and may therefore be tolerated as a result of this alignment.

For example, a graphical aid may therefore be displayed by the signal or as the signal, indicating a current angular deviation between the acquisition direction of the endoscope and the specified spatial direction. An aid may be displayed or output by signal, as the signal, or as part of the signal in order to assist the user during the alignment of the endoscope. This may be realized by corresponding arrows, color coding, and/or a bulls-eye view, for example. Corresponding displays or representations may be displayed (e.g., output) on a corresponding display device (e.g., a monitor or a head-mounted display (HMD), such as a display that is attached to a head of the respective observer or user).

The acquisition direction of the endoscope need not necessarily correspond to a central or longitudinal axis of the endoscope itself (e.g., the housing or body thereof). A corresponding angular deviation may, however, be predetermined as a parameter or parameter value.

It is thus possible to achieve a greater actual or at least perceived precision of the overlay image or of the corresponding overlay in augmented reality (AR) applications without any need for additional images or recordings of the target object (e.g., further X-ray recordings for the registration with the 3D data set). A corresponding alignment of the endoscope is sufficient, and this may be performed (e.g., achieved) easily, rapidly, in a flexible manner, and without adversely affecting the target object. It is consequently possible in a particularly simple and innocuous manner to reduce a risk of erroneous decisions resulting from an uncertainty, of which the respective user is not aware or conscious, in a spatial direction with regard to the 2D/3D registration. It is, for example, understandable and natural for a user to assume that the evidently high precision or accuracy of the registration in x- and y-directions would also apply to the z-direction likewise, even if this is not actually the case.

In a further embodiment, a robot-guided endoscope is used as the instrument. Here, likewise, a pose of the endoscope in a coordinate system of the 3D image and/or the 2D image is automatically tracked, at least up to a predetermined transformation of coordinates. Here, likewise, an overlay image is generated from an endo scope image of the target object, as recorded by the endoscope, and the 3D data set. A control signal for the robot is then generated as the signal or as part of the signal, and is used by the robot to automatically align the endoscope such that the acquisition direction thereof extends along the specified spatial direction in order to reduce a visualization error caused by the uncertainty of the 2D/3D registration in the overlay image.

In other words, the robot-guided endoscope is therefore automatically aligned (e.g., tracked) in order to give optimized visualization or image quality of the overlay image. For this purpose, a current pose of the target object may additionally be monitored and tracked, for example, and automatically taken into consideration when aligning the endoscope (e.g., when generating the control signal correspondingly). In this way, the endoscope may be aligned in a particularly rapid, precise, and reliable manner, accordingly. An optimal visualization quality of the overlay image may thus be provided in a particularly accurate and reliable manner. It is advantageous that no attentiveness or effort is required on the part of the respective user in this case, and therefore, the examination of the target object may be performed more quickly if required and with fewer distractions or less pressure for the respective user.

In a further embodiment, an endoscope is likewise used as the instrument and the pose thereof in a coordinate system of the 3D image and/or the 2D image is tracked, at least up to a predetermined transformation of coordinates. Here, likewise, an overlay image (e.g., AR image) is generated from an endo scope image of the target object, as recorded by the endoscope, and the 3D data set. A control signal for an imaging modality that is used to record the 2D image (e.g., the cited second imaging modality, such as a C-arm X-ray device) is then generated as the signal or as part of the signal. The imaging modality (e.g., the X-ray device) is automatically aligned by this control signal such that the imaging or recording direction thereof automatically extends along an acquisition direction of the endoscope, such that a visualization error, caused by the uncertainty of the 2D/3D registration, is reduced in the overlay image.

In other words, an angulation of the second imaging modality (e.g., the X-ray device) may be automatically adapted or corrected as a function of the registration uncertainty and the current pose (e.g., orientation) of the endoscope and the acquisition direction thereof. The second imaging modality is therefore automatically moved or adjusted as an aid to the respective user such that the recording direction thereof (e.g., a corresponding X-ray projection direction) extends parallel or antiparallel to a viewing direction (e.g., the acquisition direction of the endoscope). It is thereby likewise possible to minimize the visualization error in the overlay image in an accurate, rapid, and reliable manner and to reduce the pressure on the user.

In a further embodiment, an endoscope is likewise used as the instrument, and the pose thereof in a coordinate system of the 3D image and/or the 2D image is tracked, at least up to a predetermined transformation of coordinates. Here, likewise, an overlay image is generated from an endoscope image of the target object, as recorded by the endoscope, and the 3D data set. As the signal or as part of the signal, a visualization of the overlay image is then adapted in a positionally dependent manner according to a degree of the uncertainty of the 2D/3D registration (e.g., by blurring, dimming, stretching, or distorting, and/or fading out a part of the overlay image). Due to the uncertainty of the 2D/3D registration, it is likewise impossible for the endoscope image and the 3D data set to be overlaid or combined in a positionally accurate manner with one hundred percent accuracy or one hundred percent certainty. This uncertainty or inaccuracy in the overlaying (e.g., in the overlay image) may differ at various points of the overlay image in this case (e.g., depending on the position). In this case, an uncertainty of the overlay or the overlay image may, for example, be dynamically dependent on a relative alignment of the endoscope or the acquisition direction of the endoscope in relation to the specified spatial direction of greatest uncertainty of the 2D/3D registration.

If the acquisition direction of the endoscope therefore deviates, for example, by an angle α from the specified spatial direction, the overlay image may be adapted accordingly (e.g., graphically processed) in order to signal or display to the respective observer or user the degree of the uncertainty or inaccuracy (e.g., of a visualization error). The blurring may be proportional to sine(α), for example. For example, arrows or other symbols may likewise display the angular deviation and/or the specified spatial direction. In one embodiment, only the 3D data set or portions of the overlay image that are based on the 3D data set are adapted correspondingly. The endoscope image therefore remains, for example, unchanged as part of the overlay image, and only these superimposed overlay structures overlaid thereon are adapted or modified. In one embodiment, a threshold value may be predetermined for the deviation of the angular deviation (e.g., the angle α between the acquisition direction of the endoscope and the specified spatial direction). If this threshold value or threshold value angle is reached or exceeded, the overlay structures (e.g., portions of the overlay image that are based on the 3D data set) may be faded out completely. In this way, the respective observer or user may be made aware of the uncertainty of the representation in a particularly intuitive and clear manner (e.g., in a manner that is particularly easy to understand and therefore particularly reliable).

In a development, the visualization of the overlay image is only adapted in the specified spatial direction of greatest uncertainty of the 2D/3D registration. In other words, for example, the blurring of the overlay structures only takes place in or along this spatial direction (e.g., in z-direction). Equally, the overlay structures may be stretched (e.g., represented in a stretched or distorted manner, such as in only the z-direction) in order to represent or display the uncertainty in the overlay image (e.g., a resulting visualization error or a resulting visualization uncertainty). It is thereby possible in a particularly simple and particularly accurate manner to display and convey to the respective observer or user the problem that the 2D/3D registration is particularly uncertain or inaccurate in the specified spatial direction. In this case, it is possible, for example, to dispense with additional markings, superimpositions, or symbols, thereby reducing or avoiding distractions or demands on the user or observer.

In a further embodiment, a stereo endoscope is used as the instrument. A pose of the stereo endoscope in a coordinate system of the 3D image and/or the 2D image is then automatically tracked, at least up to a predetermined transformation of coordinates. Here, likewise, an overlay image is generated from a stereoscopic endoscope image of the target object, as recorded by the stereo endoscope, and the 3D data set. In this case, provision is made for generating a spatial effect in the overlay image (e.g., an impression of depth in the specified spatial direction) by a vergence or parallax between a left-hand part-image and a right-hand part-image of the stereoscopic endoscope image. By this, an improved adaptation may be achieved between the endoscope image or the stereoscopic depth location thereof and the 3D data set or portions of the overlay image generated therefrom. It is thereby possible to convey an improved impression (e.g., a more realistic impression) to the observer or user.

A plurality of embodiment variants, in which an endoscope is used, are described here. Respective configuration details or explanations described in connection with one of more of these embodiment variants also apply analogously to the other embodiment variants in a corresponding manner.

In a further embodiment, provision is made for automatically specifying, and outputting as the signal, a path along which the instrument is to be guided in order to reach a predetermined target, taking into consideration the uncertainty of the 2D/3D registration. The uncertainty is, for example, direction-dependent.

The path may be not only a series of way points or positions in this case, but may also include or specify respective orientation information (e.g., orientations or poses of the instrument that are to be adopted or adjusted at the points of the path or along the path).

The predetermined target may be, include, or indicate a desired position or pose of the instrument, a specific point of the target object, a sample collection from a specific tissue, tissue section, or part of the target object, for example, an action on a specific tissue, a specific tissue section or a specific part of the target object, and/or similar. At the same time, a structure of the target object that is derived or predetermined from the 3D data set and/or from the 2D image and which may restrict or limit possible paths and/or alignments of the instrument may be taken into consideration.

The path may be specified, for example, such that the instrument moves or is able to move along the path as little as possible in the specified spatial direction of greatest uncertainty and/or with minimal deviation between the alignment of the instrument and the specified spatial direction. It is thereby possible overall to improve or maximize a positioning accuracy of the instrument in relation to the target object or the predetermined target, and accordingly, the predetermined target may be reached with greater accuracy or reliability and, if applicable, less adverse effect on the target object. The instrument typically has a limited range of effect, for example. Due to the uncertainty of the 2D/3D registration, an additional way point or position of effect (e.g., deployment position) of the instrument may then be planned or provided as part of the path (e.g., in the specified spatial direction), such that the predetermined target (e.g., a lesion of the target object) is included in or covered by the range of effect of the instrument despite the registration uncertainty. In this case, the effect of the instrument may be or include, for example, depiction of the predetermined target, optionally with a predetermined minimal image sharpness, or also manipulation of the target object or the predetermined target (e.g., collection of a sample and/or an ablation).

In a development, a preferred direction of an effect of the instrument is taken into consideration for the purpose of specifying the path. In other words, a spatial anisotropy of the effect or range of effect of the instrument is therefore taken into consideration. For example, the instrument may be a biopsy needle for the purpose of sample collection, by which a plurality of samples may be collected along the path (e.g., in a movement direction of the biopsy needle but not in sideways directions relative thereto).

In order to provide that a sample is actually collected from the respectively predetermined target or target region, it is advantageous, for example, for the path to be planned or specified such that the instrument, while being guided along the specified path in the region of the predetermined target according to the application case (e.g., according to the shape of the predetermined target region), moves along or, for example, perpendicular to the specified spatial direction of greatest uncertainty of the 2D/3D registration. Taking the preferred direction of the instrument or the effect of the instrument into consideration, it is likewise possible by virtue of planning or specifying the path in a corresponding manner, for example, to achieve a maximum overlap between the range of effect of the instrument and the predetermined target, taking the registration inaccuracy and visualization inaccuracy or uncertainty into consideration. For example, an ablation zone in the case of a needle ablation may not be circular or spherical but elliptically elongated along an axis of an ablation needle that is used correspondingly. If, for example, tumor tissue is to be removed, the present embodiments make it possible to provide with greater probability or reliability that the tumor tissue is actually situated completely within a volume or range of effect of the ablation (e.g., within the ablation zone), and that surrounding tissue is not affected or is affected as little as possible in this case.

It is therefore possible, using the present embodiments, to specify an improved path for an interventional or surgical instrument having an effect on a target object (e.g., body tissue) that has a geometric preferred direction or spatial anisotropy. This is achieved by taking into consideration the preferred direction or anisotropy and the spatially anisotropic uncertainty or inaccuracy of the 2D/3D registration and hence of the overlay image likewise.

In a further embodiment, the instrument itself is represented in the overlay image (e.g., as an image or a model). As the signal, as part of the signal, or using the signal, the representation of the instrument and/or a range of influence or range of effect of the instrument in the overlay image is then broadened in a spatially anisotropic manner as a function of the respective local uncertainty of the 2D/3D registration. In other words, the representation of the instrument and/or a range of effect of the instrument may therefore be distorted in accordance with the uncertainty of the 2D/3D registration and thus in accordance with an uncertainty of the visualization or representation of the overlay image. Since the relevant user is typically familiar with the instrument, the type, degree, and direction of the uncertainty or of a corresponding visualization error may thus be displayed to the user in a manner that is particularly simple, intuitively understandable, and not unnecessarily distracting. If the instrument actually has, for example, a cylindrical or rod-shaped form or shape, this may be broadened (e.g., elliptically) in the overlay image according to the current alignment of the instrument in relation to the specified spatial direction. The representation of the range of effect may be adapted correspondingly.

The anisotropic broadening of the representation may equally signify that the representation of the instrument in the overlay image is surrounded by a corresponding broadening zone or uncertainty zone (e.g., a correspondingly marked spatial region). For example, a path for the instrument may then be planned or traced automatically or by the respective user. The path guides the instrument such that the entire broadened representation of the instrument or a range of effect of the instrument passes through the predetermined target (e.g., a lesion or similar) and therefore, acquires the target completely. It is thus possible to provide that despite the registration uncertainty, all possible instrument paths within a region indicated or displayed by the broadened representation actually pass through or encounter the predetermined target (e.g., the lesion or a tumor or similar). For example, if the range of effect of the instrument is smaller than the broadened representation, it is possible to plan or trace, for example, a plurality of positions of effect or deployment positions accordingly (e.g., a plurality of sample collection points or a plurality of adjacent paths through the predetermined target or in the region of the predetermined target), such that an overlap of the predetermined target with the entire broadened representation and/or with the range of effect of the instrument is provided.

If the instrument is, for example, a needle and if the uncertainty of the 2D/3D registration is relatively low in the x- and y-directions but is relatively high in the z-direction, the needle would be represented, for example, as a line during alignment in or along the z-direction, and would be represented as increasingly broad as a result of increasing deviation from this alignment. An alignment of the needle in or along the z-direction signifies in this case that a longitudinal extension direction or main extension direction of the needle runs in the z-direction.

In a further embodiment, as a function of the direction-dependent uncertainty of the 2D/3D registration (e.g., taking into consideration a preferred direction of an effect of the instrument), at least one deployment point of the instrument is specified automatically and a corresponding indication (e.g., corresponding position data), a corresponding recommendation, or a corresponding identification code is output as the signal. The deployment point in this context is therefore a position (e.g., with an associated orientation of the instrument), at which the instrument is to develop an intended effect and/or is to be positioned in order to develop an effect. If the instrument is, for example, a biopsy needle or an ablation needle, the deployment point may indicate, for example, a point or a part of the target object at which or from which a sample is to be collected by the biopsy needle or at which material or tissue is to be ablated by the ablation needle. It is therefore possible, as a function of the direction-dependent registration uncertainty, taking into consideration the direction of effect and the anisotropy of the range of effect of the instrument, to specify and output a recommendation for at least one deployment point (e.g., a position of effect or application position) for the instrument. In this way, it is possible automatically to provide in a reliable manner that the effect of the instrument actually reaches a predetermined target in spite of the registration uncertainty. Without the corresponding indication, it may otherwise be difficult for a user, due to the registration uncertainty and possible resulting visualization error, to estimate whether and if necessary with what probability the predetermined target is actually reached in the case of a respectively current positioning and alignment of the instrument.

In a further embodiment, a respectively current alignment of the instrument is automatically acquired (e.g., tracked). As a function of the acquired alignment of the instrument and the uncertainty of the 2D/3D registration, a probability that a predetermined target is reached by the instrument in the acquired alignment is automatically calculated. The calculated probability is then output as the signal or as part of the signal. It is therefore possible to calculate, for example, by a statistical analysis such as a Monte-Carlo simulation or similar, a probability with which a specific path or a combination of paths of the instrument will result in the predetermined target (e.g., a lesion or a tumor) actually being reached or a sample collection from a specific tissue region actually being achieved. This probability is then displayed to the respective user, who may adapt the path or the alignment of the instrument accordingly and/or perform an improved (e.g., more accurate) registration until a probability of reaching the target, the probability being sufficient in the respective particular case, is reached or established. The success of a respective application may thus be improved or verifiable with statistical objectivity (e.g., predicted in a clear manner). If an examination of a collected sample gives a negative result, for example, this may be classified or evaluated with reference to the probability that the sample was collected from the predetermined target tissue. The probability is established by the path that was used for the instrument at the time of the sample collection. If it is verifiably provided as a result of using the present embodiments that the probability of reaching the target is or was 100% or close to 100%, it is optionally possible to forgo a further sample collection.

In an embodiment, an uncertainty, inaccuracy, or tolerance when guiding or positioning and/or tracking the instrument may also be added as a statistically independent variable to the uncertainty of the 2D/3D registration (e.g., combined therewith). In this way, the probability of reaching the predetermined target may be calculated even more accurately and reliably. Accordingly, some or all of these uncertainties or probabilities may likewise be taken into consideration when the representation of the instrument is adapted as described above (e.g., by further broadening the representation correspondingly). It may thus be conveyed to the respective user, for example, how far and/or with what probability an actual path or an actual position of the instrument may deviate from a planned path or a planned position.

Irrespective of the embodiment variant that is used in each case, provision may be made for acquiring a plurality of 2D images consecutively (e.g., in the form of a fluoroscopy). It is then possible automatically to perform an update according to a current 2D image and a respective recording direction for the current 2D image in each case. For example, the spatial direction of greatest uncertainty of the 2D/3D registration may be specified or updated afresh in each case, the 2D/3D registration can be performed or updated afresh in each case, and/or a correspondingly updated signal may be generated and output.

A further aspect relates to a computer program product including a computer program. The computer program in this case encodes or represents a method according to the present embodiments (e.g., the method acts of at least one embodiment variant of the method). In this case, the computer program product or the computer program is designed and configured to be loaded into a storage device of a data processing device (e.g., an imaging system) and to execute the method when the computer program is executed by the data processing device. For this purpose, the data processing device may include a corresponding processor device (e.g., at least a microchip) or a microcontroller that is connected to the storage device. The computer program product may therefore include program means for executing the method. The program means may include further components that are not explicitly cited here (e.g., corresponding control commands, register references, and/or similar).

A further aspect relates to a data medium (e.g., a non-transitory computer-readable storage medium) or data store that is, for example, electronic and/or electronically readable and/or computer readable (e.g., for an imaging system). Stored on the data medium in this case is a program code that may be executed, for example, automatically by a data processing device and includes a computer program that encodes or represents at least one embodiment variant of the method (e.g., corresponding method acts) in order to effect an execution of the method (e.g., the corresponding method acts) when the computer program or program code is executed by the data processing device.

For example, at least one embodiment variant of the computer program product or the computer program included therein may therefore be stored on the data medium.

A further aspect relates to an imaging system. The imaging system has an acquisition device for acquiring a 3D data set that depicts a target object, and at least one 2D image of the target object. In this case, the 3D data set may have been recorded at an earlier time point (e.g., by another system). In this case, the acquisition of the 3D data set may signify, for example, the retrieval thereof from an electronic or computer readable data store or similar. Equally, the acquisition device itself may be designed and configured to record (e.g., measure) the 3D data set. The imaging system also includes a data processing device. The data processing device includes a processor device and a data medium that is connected thereto. The imaging system also includes an output device for outputting an automatically generated signal. In this case, the output device may be or include, for example, an interface of the data processing device, a program module of the computer program or program code, and/or a display device such as a screen or an HMD. The imaging system of one or more of the present embodiments is therefore designed and configured, for example, to perform or execute the method of one or more of the present embodiments. Accordingly, the imaging system may therefore have some or all of the properties and/or components or parts cited in connection with the other aspects of the present embodiments (e.g., in connection with the method, the computer program product, and the data medium).

The imaging system may be configured in this case as a compact system or device (e.g., a system or device that is integrated or arranged in a housing). Equally, at least some components or parts of the imaging system (e.g., therefore, the acquisition device and the data processing device) may be arranged at different locations, these being spatially distributed or spatially separate from each other. The data processing device of the imaging system (e.g., as a computer center or part of a computer center) may therefore be situated in a different room than the acquisition device. The data processing device may be arranged "on-premise" in this case. This may signify, for example, that the data processing device and the acquisition device (e.g., all components or parts of the imaging system) may be arranged on the same operational site (e.g., on the same company premises, factory premises, or hospital premises). Equally, the data processing device may, however, be, for example, a remotely located server device (e.g., a cloud server or remote server). This may then be arranged in a computer center and connected to the acquisition device of the imaging system via, for example, a wide area network (WAN), such as, for example, the Internet.

It is emphasized at this point that although the method of one or more of the present embodiments may be executed, for example, during or in preparation for an interventional or surgical action, it does not itself however include or even assume any surgical steps. Rather, the method of one or more of the present embodiments may be regarded as a method for operating an imaging system or a data processing device, where received data is processed, and output data is generated and output in the form of the signal. This may be completely separate and independent from an actual interventional or surgical application. The method may not serve to automatically effect a diagnosis.

The properties and developments specified above and in the following with respect to the method, the computer program, the data medium, and the imaging system, as well as the corresponding advantages, may be transferred analogically in either direction between these aspects of the present embodiments in each case. Included in the scope of the invention are therefore those developments of the method, the computer program, the data medium, and the imaging system having embodiments that, in order to avoid unnecessary redundancy, are not described separately and explicitly in the respective combination or for each aspect of the invention.

DETAILED DESCRIPTION

The exemplary embodiments explained below are variants of the invention. In the exemplary embodiments, the components of the embodiment variants, as described, represent in each case individual features of the invention, being regarded as independent of each other. The features respectively develop the invention independently of each other likewise and are therefore also to be considered as constituents of the invention individually or in a combination other than that shown or described. The embodiment variants as described may also be supplemented by further features of the invention described above.

Figure 1:
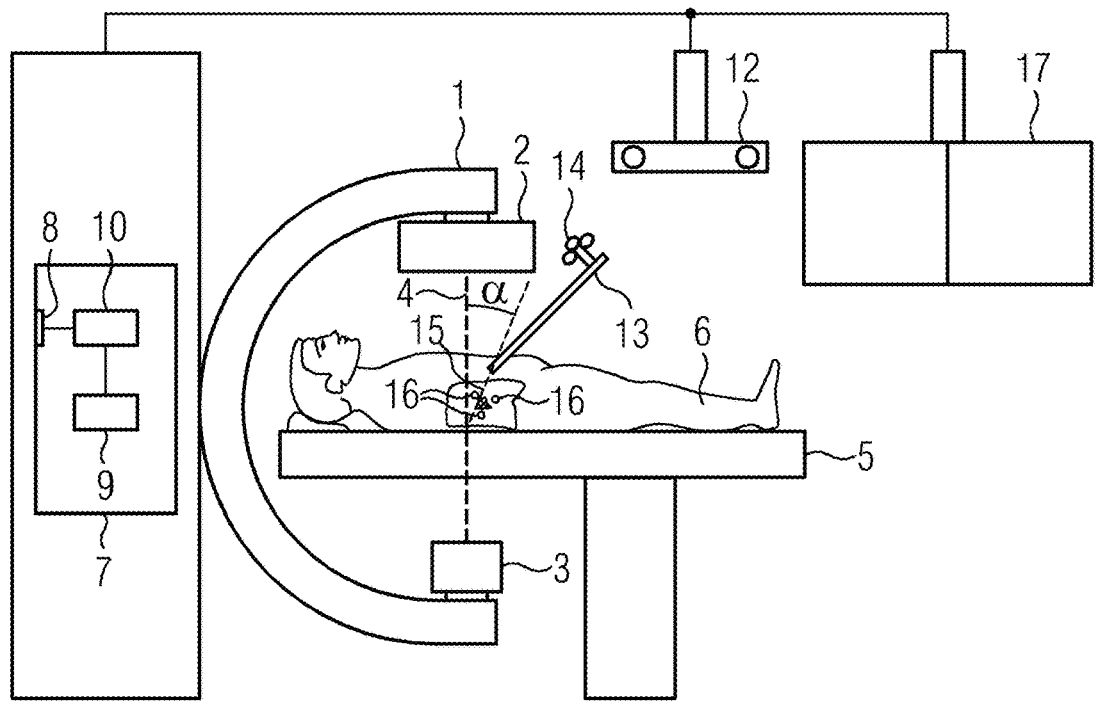
FIG. 1 shows a schematic representation of one embodiment of an imaging system.

FIG. 1 shows a schematic representation of one embodiment of an imaging system 1 configured as, for example, a C-arm X-ray device. The imaging system 1 in this case has a radiation source 3 and a detector 2 for detecting X-radiation emitted by the radiation source 3. Using the X-radiation (e.g., by the imaging system 1), a target object may be depicted along or in a recording direction 4 in this case. In this case, a patient 6 situated on a patient support 5 is depicted as a target object at least locally by the imaging system 1. The imaging system 1 also has a data processing device 7 for processing sensor data or image data provided by the detector 2 and, if applicable, further data received or acquired via an interface 8 of the data processing device 7. The data processing device 7 also has a storage device 9 and a processor device 10 that is connected to the storage device 9 and the interface 8. Stored on or in the storage device 9 in this case is a computer program (e.g., program code; instructions) that encodes or represents a method for supporting a user. This computer program or this program code may be executed by the processor device 10 in order to execute the method.

Figure 2:
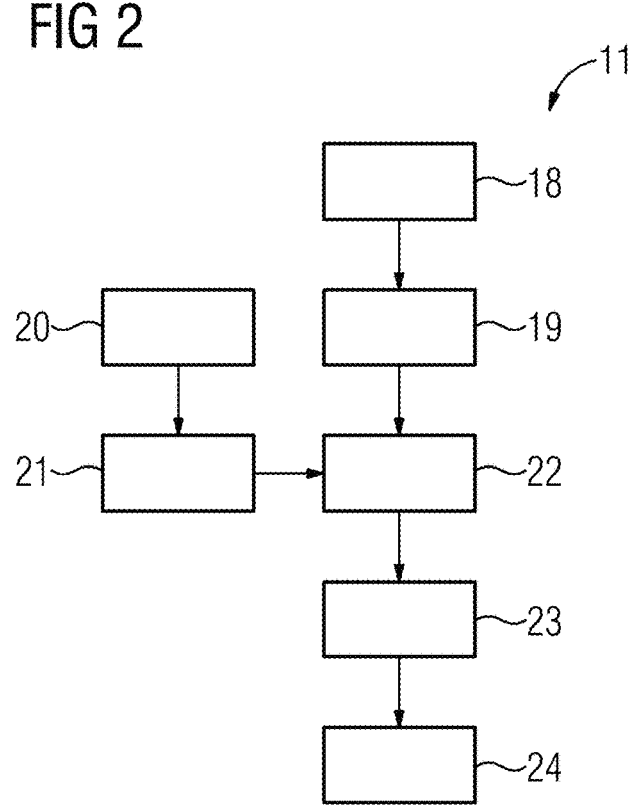
FIG. 2 shows an exemplary schematic program model of a method for supporting a user of the imaging system of FIG. 1.

FIG. 2 shows an exemplary program model 11 in the form of an extract, with schematically indicated program modules 18 to 24 for such a method for supporting a user of the imaging system 1.

The imaging system 1 in this case further includes a tracking system 12 that is configured as, for example, a stereo camera and/or for electromagnetic tracking, for example. An instrument such as a laparoscope 13 represented in FIG. 1 may be tracked by the tracking system 12. In order to allow the tracking (e.g., continuous or periodical acquisition of the laparoscope 13), this has a corresponding marker 14 in this case. Using the laparoscope 13, it is possible optically to depict the patient 6 in a viewing or acquisition direction 15 of the laparoscope 13.

Arranged in the patient 6 in this case are a plurality of patient markers 16 that may likewise be acquired by the tracking system 12 in order to specify and track a pose of the patient 6.

The imaging system 1 in this case further includes a display device 17 that is configured as a screen or monitor by way of example in FIG. 1.

A use of the imaging system 1 for supporting the user and the program model 11 illustrated in FIG. 2 are explained in greater detail below with reference to FIG. 1 and FIG. 2.

In medical or surgical applications, use is nowadays often made of augmented reality. A 3D data set (e.g., a preoperative or pre-interventional 3D volume scan of the patient 6) is acquired for this purpose by the program module 18 in this case. At least one 2D image of the patient 6 is then acquired by the program module 18 and the imaging system 1 as part of the intervention. An endoscope image and/or endoscope video of the patient 6 is acquired by the program module 18 and is recorded by the laparoscope 13 in this case. The objective is to initially generate an overlay image (e.g., an AR image) from these different sets of data.

In surgical augmented reality, for example, overlaid structures or superimpositions are in this case to be registered with the endoscope image or endoscope video (e.g., a laparoscope image or laparoscope video) as precisely as possible in relation to a real anatomy of the patient 6. Equally, registration that is as precise as possible in relation to the real anatomy of the patient 6 is necessary, for example, for navigated guidance of needles (e.g., based on laser guidance or optical navigation). For this purpose, needle paths (e.g., paths along which the needles or a corresponding instrument will be moved or guided) are often calculated based on a 2D/3D registration or 2D/2D/3D registration of one or two 2D X-ray projections (e.g., 2D X-ray images) with the 3D volume scan or a corresponding 3D data set. A further example is needle guidance with the aid of 2D or 3D ultrasound, where an algorithm computes a 2D/3D registration with a 3D ultrasound scan or with a 3D CT scan or 3D MR scan. By virtue of the 2D/3D or 2D/2D/3D registration, it is then not necessary to perform a further 3D scan during the needle intervention, or a movement update may be achieved quickly after an intraoperative scan using further X-ray or projection images recorded during the intervention.

In many cases, however, the registrations described are not equally precise in all spatial directions. For example, the case often occurs that the registration takes place with relatively high precision in two reciprocally orthogonal spatial directions. The two reciprocally orthogonal spatial directions are a designated x-direction and a designated y-direction without restricting general applicability, while a third spatial direction (e.g., a z-direction) may only be registered very inaccurately. Specifically, this case occurs, for example, if during an operation or intervention a 2D X-ray image is recorded by the imaging system 1 along the z-direction or z-axis, which then corresponds or may correspond to the recording direction 4. A previously recorded or acquired (e.g., available) 3D data set is then to be registered with this 2D X-ray image by a 2D/3D registration.

This 2D/3D registration or 2D/2D/3D registration is performed by a program module 19 in this case.

The 2D/3D registration is then used to overlay the 3D data set, or a representation derived therefrom such as, for example, a segmented mesh, onto the endoscope image by or in the form of an AR representation (e.g., by or in the form of augmented reality). Additionally or alternatively, the 2D/3D registration is used as a basis for planning the path of a needle (e.g., a biopsy needle or ablation needle or other instrument).

In this case, the program module 20 acquires and tracks the laparoscope 13 with reference to the marker 14, and the patient 6 with reference to the patient markers 16 (e.g., respective poses of the laparoscope 13 and the patient 6 are acquired and tracked by the program module 20). This provides that the acquisition direction 15 of the laparoscope 13 is therefore known and is therefore available for data processing. The recording direction 4 is also known from corresponding control parameters or operating parameters of the imaging system 1, and is therefore available for data processing. The program module 21 specifies the acquisition direction 15 relative to the recording direction 4 (e.g., an angle α between the recording direction 4 and the acquisition direction 15).

A problem is presented by the fact that the 2D/3D registration is generally relatively precise, for example, in the x-direction and in the y-direction, but is markedly less precise in the z-direction (e.g., along the recording direction 4). When generating the AR image or overlay image (e.g., when overlaying the 3D data set or overlay structures generated therefrom onto the endoscope video), this inaccuracy or uncertainty along a spatial axis or spatial direction may be very disruptive for an observer or the user, and depending on the viewing direction of the endoscope 13 (e.g., depending on the relative alignment of the acquisition direction 15) may have varying degrees of effect or noticeability. An imprecise overlay of which the user (e.g., a surgeon) is unaware conceals the danger of an erroneous decision, and in the worst case, may result in, for example, an incision being made at the wrong point of the patient 6 or a specific organ. For example, in the case of needle biopsies, it is desirable to be certain that a lesion that has been identified with the aid of the 3D data set (e.g., 3D imaging) will actually be encountered along the needle path. It is possible, for example, to allow the collection of a plurality of biopsies (e.g., samples) along the needle path, where sample positions that deviate to the side of the needle path may not, however, be examined or reached.

In a further example, an ablation zone for a needle ablation is not circular, but extends further along a needle axis than in the other directions. However, a tumor is to lie completely within a volume of the ablation zone in this case.

When planning an application path of an interventional or surgical instrument with an effect on a body tissue that has a geometric preferred direction or anisotropy, it is generally necessary to allow for a spatial anisotropy of the accuracy or certainty/uncertainty of the 2D/3D registration.

The user previously had no help or indication of the direction in which the 2D/3D registration and therefore the overlay (e.g., the overlay image or AR image) was accurately or inaccurately registered or visualized. Equally, the spatially anisotropic precision or certainty of the 2D/3D registration was not previously taken into consideration during the planning of needle paths.

One possible solution is to improve or provide a registration accuracy or registration certainty in all spatial directions by using a plurality of X-ray projection directions (e.g., a plurality of 2D X-ray images from or having different angulations) using a biplanar X-ray system, or using 3D X-ray images also during the respective intervention. However, this may result in disadvantages in a surgical workflow, a higher dosage, or exposure for the patient 6, and if applicable, the disadvantageous necessity of using a more resource-intensive and expensive imaging system 1.

In the present example, the imaging system 1 is configured as a C-arm X-ray device for intraoperative 3D imaging and 2D fluoroscopy. Optical live imaging is effected by the laparoscope 13. This has, for example, an angled lens, such that the acquisition direction 15 of the laparoscope 13 is angled relative to a direction of longitudinal extension or a shaft or housing of the laparoscope 13 (e.g., by 30°). It is intended in this case to perform, for example, a laparoscopic examination on the patient 6 lying on the patient support 5 (e.g., an OP table). For example, it is intended to resection a tumor on the liver. The user (e.g., a surgeon) uses the laparoscope 13 for this purpose. The laparoscope 13 is tracked with respect to a position and an orientation (e.g., a pose) using the tracking system 12. It is optionally possible for further surgical instruments not individually represented here (e.g., forceps, a pointer, an electro-cauterizer, and/or similar) to be acquired and tracked by the tracking system 12 or by a further tracking system. Equally, it is also possible, for example, to specify position and location of the laparoscope 13 with reference to X-ray images or fluoroscopy images recorded by the imaging system 1.

The tracking system 12 or a coordinate system of the tracking system 12 in which the laparoscope 13 is acquired and tracked is calibrated to a coordinate system of the X-ray images and 3D data set recorded by the imaging system 1. It is then possible, using a predetermined transformation of coordinates, to calculate how objects with 3D coordinates that were calculated from the X-ray images and/or from the 3D data set may be represented as overlaid in a positionally correct manner in the endoscope image recorded by the laparoscope 13 or a corresponding coordinate system.

The laparoscope 13 may be a stereo laparoscope in this case. Equally, the display device 17 may be a stereoscopic display device (e.g., a 3D monitor or a stereo head-mounted display (HMD)).

In an ideal case, the laparoscope 13 view is aligned parallel to the X-ray projection device of the imaging system 1. This provides that the acquisition direction 15 in this case is therefore aligned parallel or antiparallel to the recording direction 4. An image plane of the endoscope image is then oriented along the spatial directions x, y. In the overlay image, the virtual overlay structures derived or generated from the 3D data set may then be superimposed on the endoscope image in a positionally accurate manner (e.g., in a manner that fits exactly) by virtue of the relatively precise registration in the x- and y-directions. The described registration inaccuracy or registration uncertainty in the z-direction (e.g., along the recording direction 4) is then effectively unnoticeable or not significantly noticeable.

If the laparoscope 13 is a stereo laparoscope, it is additionally possible to generate a 3D depth impression using a vergence and/or parallax of the superimposition between a left-hand part-image and a right-hand part-image of the stereo endoscope image, where the corresponding depth direction in this case is likewise parallel to the X-ray projection direction z (e.g., the recording direction 4). The 2D/3D registration or the overlay in the overlay image may even be inaccurate here, since the eye of an observer or user does not in reality perceive small deviations or inaccuracies in a depth direction as significantly disruptive, and therefore, the inaccuracy or uncertainty in the depth direction may be tolerated in this case.

In a general case, the angle $\alpha$ between the viewing or acquisition direction 15 of the laparoscope 13 and the X-ray projection direction (e.g., the recording direction 4) is other than zero. As a result of this, the image plane of the endoscope image is no longer parallel to the spatial directions x, y. As a result of this, the greater registration uncertainty or a greater registration error in the z-direction has a direct effect on the 2D overlay of the preoperative images (e.g., proportional to $\sin(\alpha)$).

It is intended to provide the user with a way for recognizing the inaccuracy or uncertainty of the 2D/3D registration and of the corresponding overlay in the overlay image (e.g., a corresponding visualization error or a corresponding visualization uncertainty or inaccuracy) in the z-direction. It is also intended to provide the user with an aid for aligning the laparoscope 13 as above for the ideal case.

The registration uncertainty is initially specified by the program module 22 with respect to a direction and a level. Previously known methods may be used for this purpose (e.g., based on the angle $\alpha$; a relative alignment of the recording direction 4 and the acquisition direction 15 to each other, and predetermined empirical values and/or return values of a registration algorithm that is used for the 2D/3D registration and/or for the generation of the overlay image).

The overlay image is then generated by the program module 23.

A signal for aligning the laparoscope 13 is then generated and output automatically as a function of the specific registration uncertainty using the program module 24.

If the viewing direction of the laparoscope 13 (e.g., the acquisition direction 15) deviates from the recording direction 4, the overlays in the overlay image are graphically adapted or processed in order to signal the degree of the inaccuracy or uncertainty to the user. This may take place, for example, by blurring the overlay structures (e.g., proportional to $\sin(\alpha)$; by blurring in z-direction only). Further possibilities include, for example, progressive (e.g., spatially gradual) dimming of the overlays or overlay structures, superimposition of arrows and/or other symbols in z-direction, and/or stretching of the overlay structures or overlay contents in z-direction. If the directional deviation is too great (e.g., if the angle α exceeds a predetermined threshold value), the overlay structures may be faded out completely.

The imaging system 1 or a navigation system may therefore provide a graphical aid that displays a respectively current directional deviation between the recording direction 4 and the acquisition direction 15 (e.g., a magnitude of the angle α). The imaging system 1 or the navigation system further provides an aid to support the alignment of the acquisition direction 15 parallel or antiparallel to the recording direction 4. A bulls-eye representation or navigation may be provided for this purpose. Additionally or alternatively, the acquisition direction 15 may be accepted as appropriate in each case, and an angulation of the imaging system 1 (e.g., of the C-arm and hence the recording direction 4) may be moved using the aid that is provided to the respective user or may be moved automatically such that the recording direction 4 is aligned parallel or antiparallel to the acquisition direction 15.

Provision is therefore made in this case for measuring a deviation between the X-ray projection direction of the imaging system 1 (e.g., the recording direction 4) and the viewing direction of the laparoscope 13 (e.g., the acquisition direction 15). An aid is then available or used for the parallel alignment of the acquisition direction 15, and/or an aid (e.g., an automatic operation) is then available or used to align the recording direction 4. A registration uncertainty and/or visualization uncertainty may be displayed to the respective user in this case by adapting overlay contents in the overlay image correspondingly.

It is possible in this way to produce a greater precision of the overlay contents (e.g., respective overlay images in a medical augmented reality representation or application) without a plurality of X-ray projection directions (e.g., a plurality of different recording directions 4) being required for this purpose. This is achieved by an optimized relative alignment of the laparoscope 13. It is thereby possible to reduce a risk that the respective user or surgeon makes an erroneous surgical decision due to the particularly uncertain registration, of which the user or surgeon is unaware, in a spatial direction. It is also possible to realize a closer integration of the laparoscope 13 and the imaging system 1 in the form of, for example, an automatic alignment of the C-arm of the imaging system 1 based on a viewing direction or acquisition direction 15 of the laparoscope 13.

The laparoscope 13 serves merely as an example. Any other desired endoscope, camera, operation microscope, or similar may likewise be used.

Returning to the example, in which a needle is used as an instrument, it may be intended, for example, to perform a needle biopsy on the patient 6 because, for example, a suspicious lesion was found with the aid of a preoperative 3D CT or MR scan. This may be situated, for example, on a liver or a prostate of the patient 6. Needle guidance (e.g., guidance or positioning (movement) of the biopsy needle) takes place in a navigated manner in this case using, for example, laser needle guidance of the imaging system 1 or optical navigation for this purpose.

For the purpose of registering the preoperative 3D scan with a current intraoperative location of an affected organ (e.g., the liver or prostate), a 2D fluoroscopy recording is performed by the imaging system 1. Using 2D/3D registration, the preoperative 3D scan is then registered with the current location of the patient 6. Alternatively, it is possible to perform, for example, two 2D fluoroscopy recordings from different angulations and a 2D/2D/3D registration. For reasons of space (e.g., in order to avoid collisions), it may, however, occur that, for example, an angle between these two angulations may be significantly smaller than an optimal value of 90°, resulting in an anisotropic accuracy (e.g., an anisotropic or direction-dependent uncertainty) of the registration. Using the method described here, it is, however, also possible to use smaller angulations or angulation angles than the customarily recommended 40° if, for example, in the case of large or heavy patients correspondingly little space or scope for movement is available.

When performing the 2D/3D or 2D/2D/3D registration in this case, there is an inaccuracy or uncertainty that is greater along the spatial direction z than along the two spatial directions x and y.

This inaccuracy or uncertainty with regard to path planning, which is dependent on the direction of the biopsy needle and typically anisotropic, may be displayed to the respective user or doctor in the context of path planning so that the user or doctor may take this into consideration when determining the needle path. Equally, the inaccuracy or uncertainty may be taken into consideration correspondingly in the case of automatic path planning A corresponding planning tool or program module (e.g., the program module 24) may also specify a recommended depth range, a quantity of biopsies, or samples to be collected consecutively, and relative spatial distances of corresponding collection positions. Taking into consideration the registration inaccuracy or uncertainty, corresponding values are specified along a needle axis (e.g., a main extension direction of the biopsy needle) or along a the needle path.

A broadening (e.g., elliptical) of a representation of the needle in the overlay image, the broadening being dependent on the uncertainty of the registration or the needle path or on a corresponding representation, may be displayed live and, for example, intraoperatively during the needle navigation. One example is a needle guide that is overlaid as augmented reality onto an endoscope image or laparoscope video that was recorded by the laparoscope 13. Here, for example, a corresponding region of uncertainty is dissolved in the region of the needle, and the lesion is displayed virtually.

In a further example, a tumor is to lie completely within an ablation zone in the case of a needle ablation. Using the planning tool or path planning module (e.g., the program module 24), a typically anisotropic uncertainty zone that is dependent on the respective alignment of the needle path or on the needle itself is represented in the overlay image around the tumor and indicates or displays the uncertainty of the registration. It is optionally possible, as in the other examples, for a spatial uncertainty of the instrument guidance and/or the tracking system 12 to be taken into consideration and added correctly.

In this example, the ablation zone around the needle is visualized by the planning module (e.g., as a function of parameters of the respective ablation, such as a power and/or a duration, and if applicable, as a function of or with reference to a model or simulation of a corresponding tissue in the region of the ablation zone). These parameters or parameter values and a pose (e.g., positioning or placement) of the ablation needle are then selected such that as far as possible the tumor and the whole spatially anisotropic region of uncertainty around the tumor lie within the ablation zone that is represented. It is optionally possible to plan a plurality of adjacent ablation volumes until the whole certainty zone is covered collectively. This may be considered analogous to planning or providing a plurality of needle paths that do not necessarily have to be arranged or run parallel to each other in this case.

It is possible in the manner described to provide improved support for needle biopsies or other instrumental interventions or applications, if applicable, thereby resulting in fewer incorrect negative results (e.g., of needle biopsies). Needle biopsies and other instrumental applications may be more selective. Using the same or improved diagnostic possibilities, it is possible, if applicable, to reduce the number of needle punctures required. The method described also allows 2D/3D or 2D/2D/3D registrations to be used more effectively for needle guidance, whereby a dosage for an additional intraoperative 3D scan may often be avoided. Relevant support for ablation procedures is also possible, where, for example, an actual or effective ablation zone may be predicted with greater precision using the planning tool, if applicable.

In summary, a perception that there is a spatial direction that has significantly greater registration uncertainty than the other spatial directions (e.g., for the purpose of endoscope alignment and/or the planning of instrument paths) is utilized to achieve improved visualization and, if applicable, patient benefits by virtue of improved and, for example, more precise instrument guidance. In this case, a respective endoscope and/or, for example, a respective X-ray device may be aligned such that the fewest possible registration uncertainties or resulting visualization errors are noticeable for a respective observer.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for supporting a user, the method comprising:
providing a three-dimensional (3D) data set that depicts a target object;
acquiring at least one two-dimensional (2D) image of the target object;
automatically performing a 2D/3D registration of the at least one 2D image with the 3D data set;
automatically specifying a spatial direction in which the 2D/3D registration exhibits greatest uncertainty; and
automatically generating, as a function of the spatial direction, and outputting a signal for supporting an alignment of an instrument that is provided for examining the target object, such that the user is supported.

2. The method of claim 1, wherein an endoscope is used as the instrument, and
wherein the method further comprises:
automatically tracking a pose of the endoscope in a coordinate system of the 2D image;
generating at least one overlay image from at least one endoscope image of the target object, as recorded by the endoscope, and the 3D data set; and
outputting an indication to the user as the signal, the indication indicating how the user may change the alignment of the endoscope, such that an acquisition direction of the endoscope extends along the specified spatial direction, such that a visualization error, caused by the uncertainty of the 2D/3D registration, is reduced in the overlay image.

3. The method of claim 1, wherein an endoscope guided by a robot is used as the instrument, and
wherein the method further comprises:
automatically tracking a pose of the endoscope in a coordinate system of the 2D image;
generating an overlay image from an endoscope image of the target object, as recorded by the endoscope, and the 3D data set;
generating a control signal for the robot as the signal; and
using, by the robot, the control signal to automatically align the endoscope, such that an acquisition direction thereof extends along the spatial direction, such that a visualization error, caused by the uncertainty of the 2D/3D registration, is reduced in the overlay image.

4. The method of claim 1, wherein an endoscope is used as the instrument,
wherein the method further comprises:
automatically tracking a pose of the endoscope in a coordinate system of the 2D image;
generating an overlay image from an endoscope image of the target object, as recorded by the endoscope, and the 3D data set;
generating a control signal for an imaging modality that is used to record the 2D image as the signal;
automatically aligning a recording direction of the imaging modality along an acquisition direction of the endoscope, such that a visualization error, caused by the uncertainty of the 2D/3D registration, is reduced in the overlay image.

5. The method of claim 1, wherein an endoscope is used as the instrument, and
wherein the method further comprises:
automatically tracking a pose of the endoscope in a coordinate system of the 2D image;
generating an overlay image from an endoscope image of the target object, as recorded by the endoscope, and the 3D data set; and
adapting, as the signal, a visualization of the overlay image in a positionally dependent manner according to a degree of the uncertainty of the 2D/3D registration.

6. The method of claim 5, wherein the adapting of the visualization of the overlay image in the positionally dependent manner is according to a spatially anisotropic degree.

7. The method of claim 6, wherein the adapting of the visualization of the overlay image in the positionally dependent manner according to the degree of the uncertainty of the 2D/3D registration comprises blurring, dimming, stretching, fading out, or any combination thereof a part of the overlay image.

8. The method of claim 5, wherein the visualization of the overlay image is only adapted in the spatial direction of greatest uncertainty of the 2D/3D registration.

9. The method of claim 1, wherein a stereo endoscope is used as the instrument, and wherein the method further comprises:
automatically tracking a pose of the stereo endo scope in a coordinate system of the 2D image;
generating an overlay image from a stereoscopic endoscope image of the target object, as recorded by the stereo endoscope, and the 3D data set; and
generating a spatial effect in the spatial direction in the overlay image using a vergence or parallax between a left-hand part-image and a right-hand part-image of the stereoscopic endoscope image.

10. The method of claim 1, wherein a path along which the instrument is to be guided to reach a predetermined target is automatically specified and output as the signal, taking into consideration the uncertainty of the 2D/3D registration.

11. The method of claim 10, wherein a preferred direction of an effect of the instrument is taken into consideration for the purpose of specifying the path.

12. The method of claim 1, wherein the instrument is represented in the overlay image, and
wherein as or by the signal, the representation of the instrument, a range of effect of the instrument, or a combination thereof in the overlay image is broadened in a spatially anisotropic manner as a function of the respective local uncertainty of the 2D/3D registration.

13. The method of claim 1, further comprising automatically specifying, as a function of the direction-dependent uncertainty of the 2D/3D registration, at least one deployment point of the instrument, wherein a corresponding indication is output as the signal.

14. The method of claim 1, further comprising:
automatically acquiring a respectively current alignment of the instrument;
automatically calculating a probability that a predetermined target is reached by the instrument in the acquired alignment as a function of the acquired alignment of the instrument and the uncertainty of the 2D/3D registration; and
outputting the calculated probability as the signal.

15. A non-transitory computer-readable storage medium that stores instructions executable by a data processor to support a user, the instructions comprising:
providing a three-dimensional (3D) data set that depicts a target object;
acquiring at least one two-dimensional (2D) image of the target object;
automatically performing a 2D/3D registration of the at least one 2D image with the provided 3D data set;
automatically specifying a spatial direction in which the 2D/3D registration exhibits greatest uncertainty; and
automatically generating, as a function of the spatial direction, and outputting a signal for supporting an alignment of an instrument that is provided for examining the target object, such that the user is supported.

16. The non-transitory computer-readable storage medium of claim 15, wherein the non-transitory computer-readable storage medium is for an imaging system.

17. An imaging system comprising:
an acquisition device configured to acquire a three-dimensional (3D) data set that depicts a target object, and at least one two-dimensional (2D) image of the target object;
a data processor comprising a processor and a non-transitory computer-readable storage medium in communication with the processor, wherein the non-transitory computer-readable storage medium stores instructions that are executable by the processor to support a user, the instructions comprising:
providing a three-dimensional (3D) data set that depicts a target object;
acquiring at least one two-dimensional (2D) image of the target object;
automatically performing a 2D/3D registration of the at least one 2D image with the provided 3D data set;
automatically specifying a spatial direction in which the 2D/3D registration exhibits greatest uncertainty; and
automatically generating, as a function of the spatial direction, and outputting a signal for supporting an alignment of an instrument that is provided for examining the target object, such that the user is supported; and
an output device configured to output an automatically generated signal.

* * * * *